US00PP25484P3

(12) United States Plant Patent
Pavlich

(10) Patent No.: US PP25,484 P3
(45) Date of Patent: Apr. 28, 2015

(54) ***BEGONIA* PLANT NAMED 'PUFF PINK'**

(50) Latin Name: ***Begonia* hybrid**
Varietal Denomination: Puff Pink

(71) Applicant: Terra Nova Nurseries, Inc., Canby, OR (US)

(72) Inventor: John C. Pavlich, East Olympia, WA (US)

(73) Assignee: Terra Nova Nurseries, Inc., Canby, OR (US)

( * ) Notice: Subject to any disclaimer, the term of this patent is extended or adjusted under 35 U.S.C. 154(b) by 98 days.

(21) Appl. No.: 13/987,230

(22) Filed: Jul. 12, 2013

(65) Prior Publication Data

US 2015/0020268 P1 Jan. 15, 2015

(51) Int. Cl.
*A01H 5/02* (2006.01)

(52) U.S. Cl.
USPC ..... Plt./343

(58) Field of Classification Search
CPC ..... A01H 5/0238
USPC ..... Plt./343
See application file for complete search history.

(56) References Cited

PUBLICATIONS

New Plants and Flowers, Dec. 6, 2012.*

* cited by examiner

*Primary Examiner* — June Hwu
*Assistant Examiner* — Keith Robinson
(74) *Attorney, Agent, or Firm* — Klarquist Sparkman, LLP

(57) ABSTRACT

A new and distinct form of *Begonia* plant characterized by attractive dark chocolate brown leaves with green veins, numerous double pink flowers, an upright habit when young, becoming decumbent with maturity, an extremely long bloom time, a caudiciform base, and excellent vigor.

1 Drawing Sheet

Botanical denomination: *Begonia* hybrid.
Variety designation: 'Puff Pink'.

BACKGROUND OF THE INVENTION

The present invention relates to a new and distinct cultivar of *Begonia*, of the family Begoniaceae, and given the cultivar name, 'Puff Pink'. The new cultivar originated from a cross between a NONSTOP MOCCA Mix *Begonia*, an unnamed, unpatented tuberous *Begonia*, as the seed parent and *Begonia dregei* 'Richardsiana', an unpatented semi-tuberous *Begonia*, as the pollen parent. This selection is uniquely characterized by:

1. attractive dark chocolate brown leaves with green veins,
2. numerous double pink flowers,
3. an upright habit when young, becoming decumbent with maturity,
4. an extremely long bloom time,
5. a caudiciform base, and
6. excellent vigor.

Compared to the seed parent, a NONSTOP MOCCA *Begonia*, the new cultivar has a larger habit with smaller and more numerous flowers that bloom over a much longer period.

Compared to the pollen parent, *Begonia dregei* 'Richardsiana', the new cultivar has larger, darker leaves, larger flowers that are double rather than single and pink rather than white, and no silver spots on the leaves.

Compared to the pink flowered *Begonia×hiemalis* types (unnamed, unpatented plants), the new cultivar has dark foliage with green veins rather than green leaves.

The new variety has been reproduced only by asexual propagation (leaf and stem cuttings and tissue culture). Each of the progeny exhibits identical characteristics to the original plant. Asexual propagation by micropropagation as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows a two year old plant of the new cultivar in a warm greenhouse in June in full bloom in Canby, Oreg.

DETAILED PLANT DESCRIPTION

The following is a detailed description of the new *Begonia* cultivar based on observations of 18-month-old specimens grown in two gallon containers in a warm greenhouse in early April in Canby, Oreg. Canby is Zone 8 on the USDA Hardiness map. Temperatures range from a high of 95° F. in August to 32° F. in January. Normal rainfall in Canby is 42.8 inches per year. The color descriptions are all based on The Royal Horticultural Society Colour Chart, 5$^{th}$ edition, 2007.

Plant:

*Type*.—Herbaceous, caudiciform perennial.
*Form*.—Upright when young, caulescent, becoming decumbent with maturity.
*Cold hardiness*.—USDA Zone 10.
*Size*.—Grows to 28 cm tall and 31 cm wide.
*Vigor*.—Excellent.
*Roots*.—Rooting initiates in two weeks, roots White NN155C in color.

Stem:

*Type*.—Upright in the first season, becoming decumbent with age.

*Size*.—Grows to 21 cm long and 7 mm wide (mature stems will grow to 45 cm long and 12 mm wide if left on the plant).

*Internodes*.—From 7 mm to 4 cm long.

*Surface*.—Glabrous.

*Color*.—Grey Brown N199A.

Leaf:

*Type*.—Simple.

*Arrangement*.—Alternate.

*Shape*.—Obliquely ovate.

*Leaf strength*.—Excellent.

*Margins*.—Coarsely serrate, with 5 to 6 shallowly triangular lobes.

*Apex*.—Acute to acuminate.

*Base*.—Oblique and truncate.

*Venation*.—Palmate, Green 143A topside, Yellow Green 144B bottom side.

*Blade size*.—Grows to 5.5 cm wide and 10.5 cm long.

*Surface texture*.—Sparsely pubescent on top and glabrous on bottom.

*Stipules*.—Deciduous, ovate, 7 mm long and 5 mm wide, apex acute and cuspidate, base clasping, entire, both sides glabrous, both sides Yellow Green 145A.

*Petiole description*.—Grows to 6 cm long and 3 mm wide, succulent, sparsely pubescent, Greyed Red 178B.

*Leaf color*.—Top side closest to Brown 200A with veins Green 143A; bottom side Greyed Purple N186D with veins Yellow Green 144B.

Inflorescence:

*Type*.—Axillary, bisexual, cymose.

*Number of flowers per cyme*.—3 to 4.

*Peduncle description*.—Grows 4 cm long and 3 mm wide, glabrous, fleshy, moderately strong, Greyed Orange 165B; with 2 opposite, dehiscent petiolate leaf-bracts below each cyme, ovate, cupped, grow to 10 mm wide and 12 mm long, margins entire and pubescent, tip acute, both sides glabrous, both sides Yellow Green 146C.

*Pedicel description*.—Grow to 25 mm long, 2 mm wide, fleshy, glabrous, Red 39A, moderately strong.

*Bloom period*.—Spring to early winter in Canby, Oreg.

Flower bud:

*Size*.—2 cm long and 2.5 cm wide prior to opening.

*Shape*.—Teardrop.

*Surface texture*.—Glabrous.

*Color*.—Red 49C.

Flower:

*Type*.—Monoecious, bilaterally symmetrical.

*Pistillate flower*.—None seen.

*Staminate flower*.—1.7 cm deep and 5.5 cm wide, 2 large outer tepals, 29 mm long and 30 mm wide, orbicular, spongy, margin entire, tip obtuse, base obtuse, glabrous on both sides, about 20 to 37 inner tepals grow to 25 mm long and 20 mm wide, decline in size to the middle, mostly obovate, entire, tip mostly acute, base attenuate, all but innermost tepals both sides between Red Purple 55A and 55B, small inner tepals White N155B on bottom half and 55C on top half on both sides; no stamen.

*Fragrance*.—None.

*Lastingness*.—A cyme blooms for about 2 weeks on the plant, flowers are self-cleaning.

Fruit and seed: None, sterile.

Diseases and pests: The new cultivar is typical to the genus. No known resistances to pests or diseases. No problems have been found in Canby, Oreg.

I claim:

1. A new and distinct form of *Begonia* plant as hereby illustrated and described.

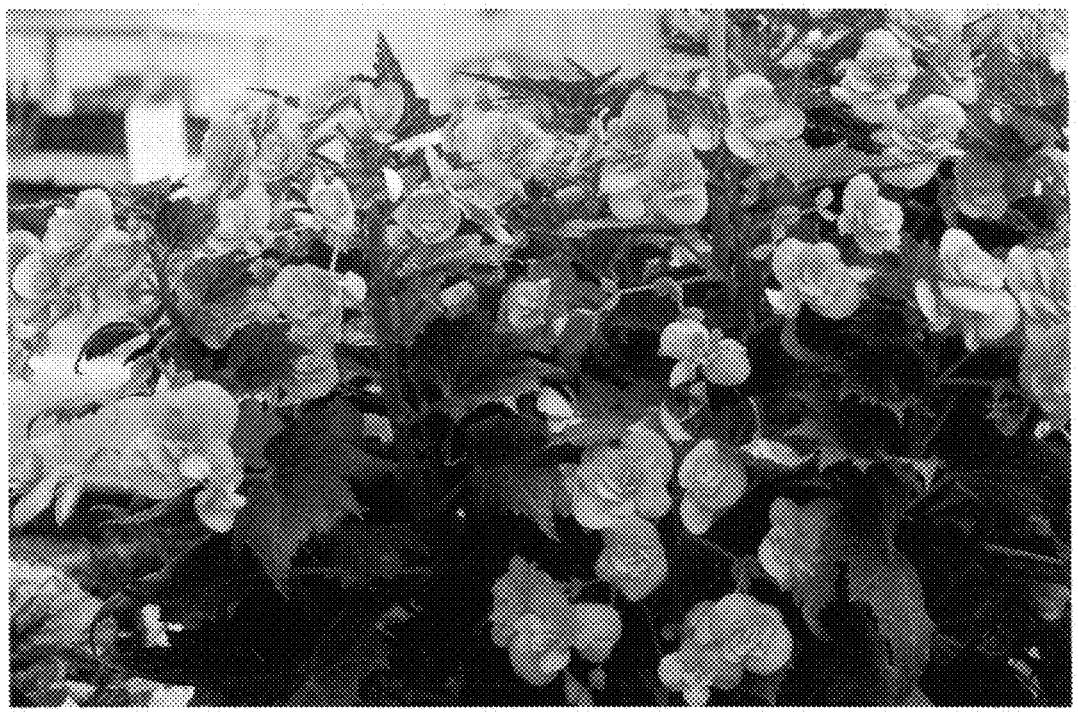

* * * * *